United States Patent [19]

Nalette et al.

[11] Patent Number: 5,073,505

[45] Date of Patent: Dec. 17, 1991

[54] ELUANT STORAGE AND PREPARATION APPARATUS AND METHOD FOR USING THE SAME IN A ZERO GRAVITY ENVIRONMENT

[75] Inventors: Timothy A. Nalette, Tolland; John W. Steele, Torrington, both of Conn.

[73] Assignee: United Technologies Corporation, Hartford, Conn.

[21] Appl. No.: 544,765

[22] Filed: Jun. 27, 1990

[51] Int. Cl.[5] .......................... G01N 1/18; G01N 1/10; C22C 38/28; C22C 38/24
[52] U.S. Cl. .................................... 436/178; 436/179; 422/68.1; 422/70; 210/660; 210/681
[58] Field of Search ............. 422/68.1, 70; 436/179, 436/150, 52, 178; 210/805, 806, 807, 660, 661, 681

[56] References Cited

U.S. PATENT DOCUMENTS

| | | | |
|---|---|---|---|
| 3,846,074 | 11/1974 | Tulumello et al. | 422/70 |
| 4,148,610 | 4/1979 | Miller, Jr. et al. | 436/179 |
| 4,610,170 | 9/1986 | Ekholm et al. | 436/179 |
| 4,794,806 | 1/1989 | Nicoli et al. | 436/179 |
| 4,868,129 | 9/1989 | Gibbons et al. | 436/179 |

Primary Examiner—Robert J. Hill, Jr.
Assistant Examiner—William K. Y. Chan
Attorney, Agent, or Firm—Alan C. Cohen; Pamela J. Mercier

[57] ABSTRACT

The present invention is related to a technique for storing concentrated eluant, preparing dilute eluant, and reclaiming water used for dilution. The invention uses stored concentrated eluant which is diluted using a sample loop coupled with a dilute eluant reservoir. Water is used for dilution and is reclaimed using a mixed ion exchange bed. The use of concentrated eluant and reclaimable water significantly reduces storage needs.

11 Claims, 1 Drawing Sheet

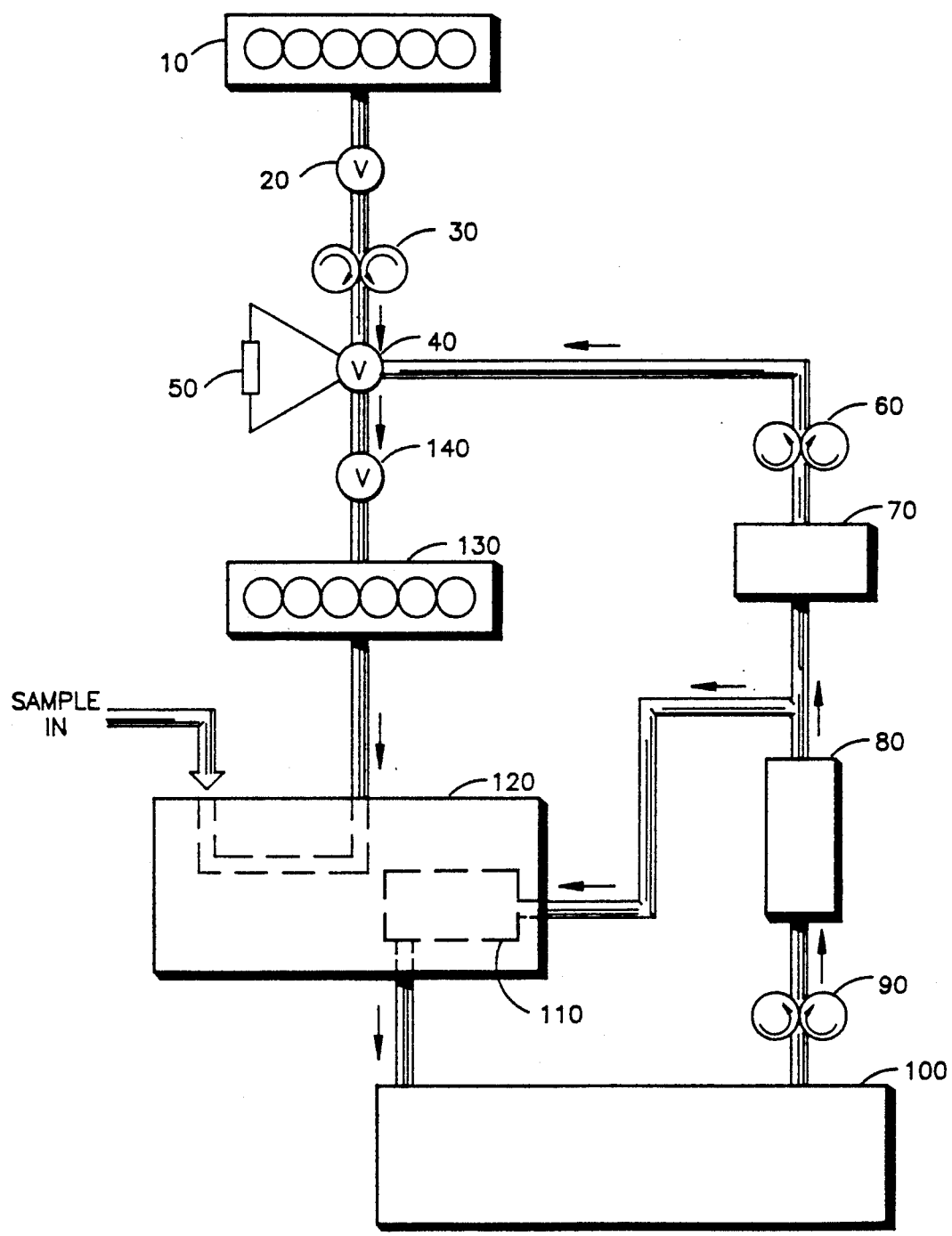

ELUANT STORAGE AND PREPARATION APPARATUS AND METHOD FOR USING THE SAME IN A ZERO GRAVITY ENVIRONMENT

CROSS REFERENCE

This application relates to copending, U.S. patent application Ser. No. 07/544,766, for TOTAL ORGANIC HALOGEN ANALYZER, filed on June 27, 1990; U.S. patent application Ser. No. 07/544,764 for AUTOMATED BIOLUMINESCENCE MICROBIAL MONITOR, filed June 27, 1990; U.S. patent application Ser. No. 07/544,767, for ZERO GRAVITY COMPATIBLE TOTAL ORGANIC AND INORGANIC CARBON ANALYZER, filed June 27, 1990; U.S. patent application Ser. No. 07/544,763, for ZERO GRAVITY PURGE AND TRAP FOR MONITORING VOLATILE ORGANIC COMPOUNDS, filed June 27, 1990 and U.S. patent application Ser. No. 07/544,768, for ZERO GRAVITY COMPATIBLE TOTAL ORGANIC AND INORGANIC CARBON ANALYZER, filed June 27, 1990, for commonly assigned.

TECHNICAL FIELD

The invention relates to an apparatus for storing and preparing eluant, and especially to an apparatus for storing concentrated eluant and preparing dilute eluant.

BACKGROUND ART

Water quality monitoring is necessary for numerous applications, especially if the water is to be used for human consumption. One analysis technique conventionally used for water quality monitoring is ion chromatography. This technique is often utilized for the detection of the chemical groups: monovalent and divalent cations, halides, transition metals, organic acids, and low molecular weight alcohols and amines (hereafter referred to as chemical groups).

The analysis requires a packed sorbent column capable of separating compounds in solution and an eluant mobile phase (hereafter referred to as eluant) to liberate the absorbed chemical compounds from the sorbent column and carry them into the detector. The eluant, generally aqueous salt solutions of 0.5 to 2.0 mM (millimolar) concentrations, is typically prepared manually as needed for analysis.

In applications where the eluant can not be readily supplied, such as in long term submarine or space missions, it is necessary to prepare the eluant, in advance, for the entire mission. Typically, approximately 200 cc (cubic centimeters) of eluant is required for each chemical group analysis. On a space mission, for example, there may be two complete chemical group analyses planned per day with six chemical groups to be analyzed. As a result, a minimum of approximately 2.5 liters (L) of eluant must be available, in storage, for each day of the mission. A 90 day mission would require approximately 225 L of eluant to be stored which is a severe expendable penalty. Additional concerns, including storage constraints, launch and resupply costs, size, weight, expendable use, and recyclability must also be taken into consideration in these applications.

Since weight and size constraints among others, are very important, what is needed in the art is an apparatus and process for efficiently preparing eluant from concentrate and reclaiming the water used in the preparation for subsequent use.

DISCLOSURE OF INVENTION

The present invention relates to an apparatus for efficiently storing concentrated eluant, preparing dilute eluant, and recycling water used for diluting the eluant. Further disclosed is a process for using the present apparatus to prepare dilute eluant for use in water quality analysis. The apparatus is comprised of a concentrated eluant reservoir, a sample loop, means for introducing concentrated eluant into the sample loop, a means for introducing water into the sample loop, a dilute eluant reservoir, a water reservoir, a means for analyzing chemical groups, a means for removing ions, and a means for detecting ions.

Concentrated eluant is transported from the concentrated eluant reservoir into a sample loop. Water is introduced through the sample loop from the water reservoir, flushing the concentrated eluant from the sample loop into the dilute eluant reservoir. Additional water is then added to the dilute eluant reservoir to prepare the desired concentration of the eluant. The dilute eluant is used in a process for analyzing the chemical groups. A spent eluant stream, a by-product of the analysis, is intimately contacted with the means for removing ions, thereby reclaiming the water. A means for detecting ions is used to determine when acceptable water quality has been achieved.

The foregoing and other features and advantages of the present invention will become more apparent from the following description and accompanying drawing.

BRIEF DESCRIPTION OF DRAWINGS

The Figure is a schematic of a possible embodiment of the eluant preparation apparatus of the present invention.

BEST MODE FOR CARRYING OUT THE INVENTION

As shown in the Figure, which is meant to be exemplary not limiting, the eluant preparation apparatus of the present invention is composed of: a concentrated eluant reservoir (10), valves (20, 40, 140), pumps (30, 60, 90), a means for removing ions (80), a means for detecting ions (110), a water reservoir (70), a sample loop (50), dilute eluant reservoir (130), and a means for analyzing chemical groups (120).

The process for preparing the eluant consists of transporting concentrated eluant from the concentrated eluant reservoir (10) into the sample loop (50). Water from the water reservoir (70) flushes the concentrated eluant out of the sample loop (50) into the dilute eluant reservoir (130). Sufficient water is then added to the dilute eluant reservoir (130) to attain the desired concentration of eluant to be used for a chemical group analysis in the means for analyzing chemical groups (120). The means of analyzing chemical groups (120) produces a spent eluant stream. This passes through the means for removing ions (80) producing an essentially deionized water stream. The water then passes through the means for detecting ions (110) to verify the spent eluant stream is essentially deionized. The reclaimed water returns to the water reservoir (70).

The concentrated eluant reservoir (10) can be any means conventionally known in the art. Since various types of eluant are used when performing analyses for different chemical groups, such as sodium carbonate and sodium bicarbonate for anions, hydrochloric acid for monovalent cations, water alone for carbonate, and octane sulfonic acid for organic acids, it is preferred that the concentrated eluant reservoir (10) contain separate compartments or modules (hereafter referred to as modules) for each eluant to be used. The number of modules is dependant on the number of different eluants needed for the various analyses to be preformed. For example, water quality monitoring typically uses six eluants, and therefore, six modules are sufficient. Empty concentrated eluant modules are replaced as needed.

If the eluant preparation apparatus is to be employed in a zero gravity environment, the concentrated eluant reservoir (10) must be capable of being used in zero gravity (hereafter referred to as zero gravity compatible). Means for making the concentrated eluant reservoir zero gravity compatible include any means conventionally known in the art, such as bladders or other flexible containers, and the use of pressure. Bladders are preferred due to convenience; increasing the pressure around the bladder causes the contents of the bladder to exit the bladder as the bladder constricts. If concentrated eluant within the compartments is stored in bladders, venting requirements during emptying and filling of the modules are eliminated. Any flexible bladder which is inert and noncontaminating can be used.

From the concentrated eluant reservoir (10), the eluant is transported to the sample loop (50) through valves (20) and (40). These valves can be any means conventionally known in the art for introducing the concentrated eluant to the sample loop (50), such as series of pipes and simple or multi-port valves.

The valve (40) diverts the eluant into the sample loop (50) where a fixed sample size of eluant can be determined. Water, including reclaimed water, is then transported through the sample loop (50) from the water reservoir (70), flushing the concentrated eluant from the sample loop (50).

The water reservoir (70) can be any means for storing water conventionally known in the art. Yet, for zero gravity use, the water reservoir (70) must be zero gravity compatible. A container with a flexible internal bladder is preferred, although other conventional methods for providing zero gravity compatibility can be used. The size of the bladder should be sufficiently large to store the water content of the dilute eluant reservoir (130). For example, assuming that a six compartment concentrated eluant reservoir (10) needed is for the analysis of six chemical groups that and approximately 200 cc of diluted eluant is needed per analysis, the amount of water needed for one full analysis and therefore the size of the reservoir, is approximately 1.2 L. The water is preferably deionized water, but can be any water which does not degrade or interfere with the eluant or chemical groups analysis.

The flushed eluant and the water are directed into the dilute eluant reservoir (130). The dilute eluant reservoir (130) is similar to the concentrated eluant reservoir (10), preferably containing separate modules for each eluant to be stored. The number of modules is equal to number of modules in the concentrated eluant reservoir (10) so that each type of eluant can be stored separately for future use in the means for analyzing chemical groups (120). Again, for use in a zero gravity environment any means which is zero gravity compatible can be employed.

Once the flushed eluant and water are in the dilute eluant reservoir (130), the flushed eluant is diluted to the concentration needed for the specific chemical group analysis for which it will be used. The dilute eluant reservoir (130) stores the dilute eluant for use in the analyzer The size of the modules in the dilute eluant reservoir (130) can be related to the concentration of the eluant. The modules are sufficiently large to hold the flushed eluant and the amount of water necessary to dilute the eluant to the desired concentration.

From the dilute eluant reservoir (130), the eluant enters the means for analyzing chemical groups (120). Depending on the type of chemical group analysis, the eluant can either be combined with the chemical group, "analyte", in or prior to the means for analyzing chemical groups (120). Any means for analyzing chemical groups (120) conventionally known in the art which uses eluant can be used, such as an ion chromatograph.

The stream exiting the means for analyzing chemical groups (120) typically contains used, eluant (hereafter referred to as spent eluant), water and analytes. The spent eluant and the analytes are typically in the form of ions. The spent eluant stream can then either be stored in the spent eluant reservoir (100) or deionized in the means for removing ions (80). The spent eluant stream is intimately contacted with the means for removing ions (80). The means for removing ions (80) can be any means capable of removing ions from, "deionizing", the spent eluant stream. A strong acid/strong base mixed ion exchange bed, such as sulfonated polystyrene and tetra methyl ammonium styrene resin, can be used in this application. In such a bed, when the spent eluant stream is intimately contacted with the bed, the ions in the stream chemically absorb into the bed, allowing the water to pass, deionized.

A recycle loop with a means for detecting ions (110) is used to determine when the spent eluant stream is essentially deionized. The means for detecting ions (110) can be any means conventionally known in the art capable of detecting ions, such as a conductivity detector or cell. The reclaimed water is then returned to the water reservoir (70). The conductivity detector can be any detector capable of measuring the conductivity of a flowing stream, with a sensitivity of at least 0.01 micromhos, such as the standard means for detecting ions conventionally used in the ion chromatography industry. A conductivity of about 0.10 micromhos or less is sufficient to permit the reuse of reclaimed water.

This process allows for automation and zero gravity compatibility for eluant preparation with a light weight, low volume, apparatus. Additionally, since the eluant is stored in the concentrated form, microbial growth problems are minimized.

Although this invention has been shown and described with respect to detailed embodiments thereof, it will be understood by those skilled in the art that various changes in form and detail thereof may be made without departing from the spirit and scope of the claimed invention.

We claim:

1. A zero gravity compatible system for chemical group analysis, which comprises:
   a. a concentrated eluant reservoir for storing concentrated eluant comprising at least one bladder;
   b. a sample loop, in flow communication with said concentrated eluant reservoir and means for introducing water therein;
   c. a dilute eluant reservoir, in flow communication with the sample loop, for receiving and storing eluant from the sample loop, said dilute eluant reservoir having at least one bladder having a means for receiving said eluant from the sample loop, means for receiving water and a means for releasing dilute eluant;

d. a means for introducing at least one ionizable chemical group to the dilute eluant;

e. a means for analyzing said chemical group in the dilute eluant in flow communication with said dilute eluant reservoir and comprising a exiting means for the dilute eluant;

f. a means for removing ions from the dilute eluant from said exiting means, so as to reclaim the water, in flow communication with said exiting means;

g. a means for detecting ions in the reclaimed water so as to ensure that the reclaimed water is essentially deionized; and h. a water reservoir in flow communication with the means for detecting ions in the reclaimed water and the sample loop and the dilute eluant reservoir, for storing water and the reclaimed water.

2. An apparatus as in claim 1 wherein the means for analyzing chemical groups is an ion chromatograph.

3. An apparatus as in claim 1 wherein the means for removing ions is a strong acid/strong base mixed ion exchange bed.

4. An apparatus as in claim 3 wherein the strong acid/strong base mixed ion exchange bed is sulfonated polystyrene and tetra methyl ammonium styrene resin bed.

5. An apparatus as in claim 1 wherein the means for detecting ions is an on line conductivity cell.

6. A zero gravity compatible system for chemical group analysis, which comprises:

a. a concentrated eluant reservoir for storing concentrated eluant comprising at least one bladder;

b. a sample loop, in flow communication with said concentrated eluant reservoir and means for introducing water therein;

c. a dilute reservoir, in flow communication with the sample loop, for receiving and storing eluant from the sample loop, said dilute eluant reservoir having at least one bladder having a means for receiving said eluant from the sample loop, means for receiving water and a means for releasing dilute eluant;

d. a means for introducing at least one ionizable chemical group to the dilute eluant;

e. a means for analyzing said chemical group in the dilute eluant in flow communication with said dilute eluant reservoir and comprising a exiting means for the dilute eluant;

f. a strong acid/strong base mixed ion exchange bed for removing ions from the dilute eluant from said exiting means, so as to reclaim the water, in flow communication with said exiting means;

g. a means for detecting ions in the reclaimed water so as to ensure that the reclaimed water is essentially deionized; and h. a water reservoir in flow communication with the means for detecting ions in the reclaimed water and the sample loop and the dilute eluant reservoir, for storing water and the reclaimed water.

7. A process for storing, preparing and using eluant in chemical group analysis, which comprises:

a. introducing concentrated eluant to a sample loop;

b. flushing the concentrated eluant form the sample loop with water;

c. introducing the flushed eluant and water into a dilute eluant reservoir;

d. diluting the flushed eluant with water to a concentration needed for a specific chemical group analysis forming a dilute eluant;

e. introducing an ionizable chemical group to the dilute eluant;

f. analyzing for a chemical group in the dilute eluant;

g. deionizing the analyzed dilute eluant by passing the analyzed dilute eluant through a means for removing ions from the analyzed dilute eluant and reclaiming the water and said process is performed in a zero gravity environment.

8. A method as in claim 7 wherein the analysis process uses an ion chromatograph.

9. A method as in claim 7 wherein the means for removing ions is a strong acid/strong base ion exchange bed.

10. A method as in claim 9 wherein the strong acid/strong base ion exchange bed is sulfonated polystyrene and tetra methyl ammonium styrene resin bed.

11. A method as in claim 7 wherein the water is deionized water.

* * * * *

UNITED STATES PATENT AND TRADEMARK OFFICE
CERTIFICATE OF CORRECTION

PATENT NO. : 5,073,505

DATED : December 17, 1991

INVENTOR(S) : Timothy A. Nalette and John W. Steele

It is certified that error appears in the above-identified patent and that said Letters Patent is hereby corrected as shown below:

Claim 6, Column 5, Line 41, after "dilute" insert --eluant--

Signed and Sealed this

Eighteenth Day of May, 1993

Attest:

MICHAEL K. KIRK

*Attesting Officer*  Acting Commissioner of Patents and Trademarks